Oct. 19, 1971 W. A. WARRINER Plant Pat. 3,080
ROSE PLANT
Filed Aug. 6, 1969
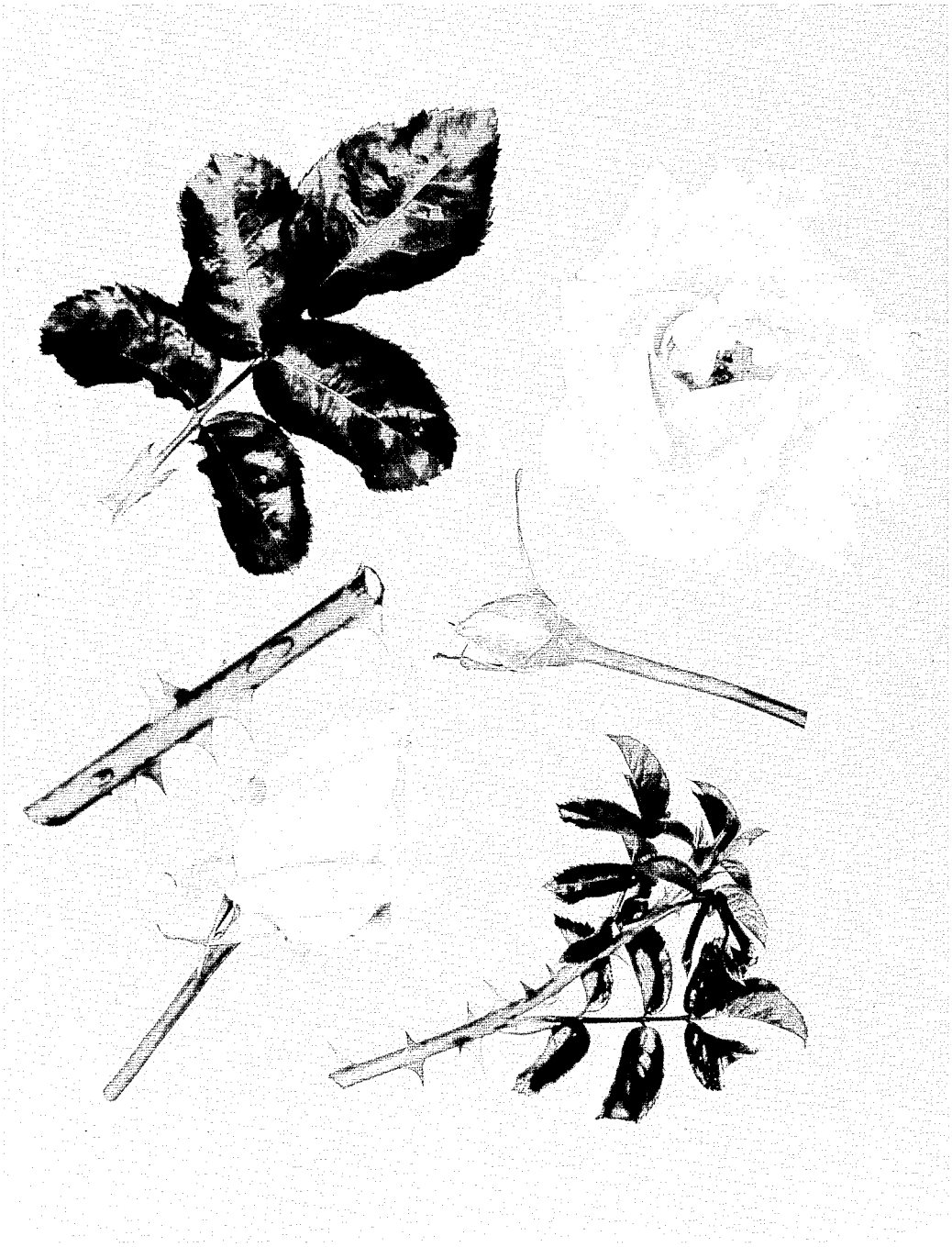
Inventor
Wm. A. Warriner
By: Robb & Robb
Attorneys

United States Patent Office

Plant Pat. 3,080
Patented Oct. 19, 1971

3,080
ROSE PLANT

William A. Warriner, Newark, N.Y. assignor to
Jackson & Perkins Company, Newark, N.Y.

Filed Aug. 6, 1969, Ser. No. 848,124
Int. Cl. A01h *5/00*
U.S. Cl. Plt.—15 1 Claim The present invention relates to a new and distinct variety of rose plant of the hybrid tea class, which was originated by me by crossing the rose variety known as "South Seas" (Plant Pat. No. 2,184) with the rose variety known as "King's Ransom" (Plant Pat. No. 2,103), the former being the seed parent and the latter being the pollen parent.

The primary object of this breeding was to produce a new and improved rose variety which is comparable to the parent variety "King's Ransom," but which bears flowers of larger size and having a more intense flower color. This objective was fully achieved, along with other desirable improvements, as evidenced by the following unique combination of characteristics which are outstanding in the new variety and which distinguish it from its parents, as well as from all other rose varieties of which I am aware:

(1) A vigorous and well-branched habit of growth;
(2) Attractive green foliage, with the new foliage being darker in color than in the parent variety "King's Ransom" and being Victoria Lake in color;
(3) A free blooming habit throughout the season; and
(4) An ovoid bud form, said buds being basically yellow in color but heavily overlaid with Garnet Brown as the sepals unfold, and opening to high-centered flowers of pale Lemon Yellow color in the half-open stage, and said flowers maintaining a distinctive and attractive pale yellow color as they fully open.

Asexual reproduction of my new variety by budding, as performed at Wasco, Calif. shows that the aforementioned characteristics and distinctions come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of the new rose variety, with color terminology in accordance with Ridgway's Color Standards and Nomenclature except where general color terms of ordinary dictionary significance are obvious:

Parentage: Seedling.
*Seed parent.*—"South Seas."
*Pollen parent.*—"King's Ransom."
Classification:
*Botanic.*—Rosa hybrid.
*Commercial.*—Hybrid tea.
Propagation: Holds its distinguishing characteristics through succeeding propagations by budding.

*Flower*

(Observations made from specimens grown at Newark, New York, in the afternoon during late June.)
Blooming habit:
*Recurrent.*—Continuous.
Bud:
*Size.*—Large; from 1¼ inches to 1½ inches.
*Form.*—Pointed ovoid.
*Color.*—When sepals first divide—Garnet Brown, Plate 1, 3 k. As sepals unfold—Strontium Yellow, Plate 16, 23′ under sepals. When half-blown—Inside of petals—Pale Lemon Yellow, Plate 4, 23 b. Reverse of petals—Picric Yellow, Plate 4, 23 d.

*Sepals.*—Lightly appendaged; hairy edge. Color—Inside—Apple Green, Plate 17, 29′, covered with white tomentum. Outside—Bice Green, Plate 17, 29′ k.
*Receptacle.*—Color—Apple Green, Plate 17, 29′. Shape—Broad at top and funnel at base. Size—Large. Surface—Smooth; glossy.
*Peduncle.*—Length—Long. Surface—Smooth, few prickles. Strength—Stiff; heavy. Color—Biscay Green, Plate 17, 27′ i.
*Opening.*—Outer petals curl slightly.
Bloom:
*Size.*—Large; about 5 inches.
*Borne.*—Both single and several together.
*Stems.*—Long.
*Form.*—High-centered; outer petals lightly quilled; center petals loosely arranged.
*Petalage.*—Number of petals under normal conditions—30.
*Color.*—Center of flower—Upper side of petals—Lemon Yellow, Plate 4, 23, lightened toward outer edges to Martius Yellow, Plate 4, 23, f. Reverse of petals—Pale Lemon Lellow, Plate 4, 23 b. lightened toward outer edge to Martius Yellow, Plate 4, 23 f. Outer petals—Upper side—Same as center of flower. Base of petals—Lemon Yellow, Plate 4, 23. General tonality from a distance—Pale Lemon Yellow. Discoloration—First day—No change. Third day—Base of petals Pale Lemon Yellow, Plate 4, 23 b, lightened toward outer edge to Sulphur Yellow, Plate 5, 25 f.
*Fragrance.*—Slight.
Petals:
*Texture.*—Thick; leathery.
*Surface.*—Inside—Satiny. Reverse—Satiny.
*Shape.*—Round.
*Form.*—Tips slightly recurved.
*Arrangement.*—Loosely imbricated.
*Persistence.*—Drop off cleanly.
*Lasting quality.*—On the plant—Very long. As cut flower—Very long.

*Reproductive organs*

Anthers: Medium Size; many; regularly arranged around styles. Color—Yellow.
Filaments (threads): Long. Color—Yellow.
Pollen: Color—Gold-yellow.
Styles: Loosely separated; uneven length; short; thin.
Stigmas: Color—Yellow.
Ovaries: All enclosed in calyx.
Fruit: None observed.

*Plant*

Form: Bush.
Growth: Vigorous; well-branched.
Foliage:
*Leaves.*—Compound of 5 leaflets on mid-stem leaves.
*Leaflets.*—New foliage—Victoria Lake, Plate 1, 1 m. Old foliage—Upper side—Forest Green, Plate 17, 29′ m. Under side—Bice Green, Plate 17, 29′ k. Shape—Broadly oval. Texture—Upper side—Semi-glossy. Under side—Smooth. Ribs and veins—Ordinary. Edge—Serrated. Serration—Single; small. Petiole (rachis)—Color—Green. Under side (lower leaves)—Have 3 or 4 relatively large thorns, approximately ⅛ inch. Stipules—Long; mostly adnate; tips perpendicular to rachis.

*Disease resistance.*—Resistant to mildew and blackspot, as determined by comparison with other rose varieties grown under the same normal conditions at Newark, N. Y.

Wood:

*New wood.*—Color—Light Green. Bark—Smooth.

*Old wood.*—Color—Green. Bark—Smooth.

Thorns:

*Thorns.*—Quantity—On main stalks from base—Few. On laterals from stalk—Few. Form—Broad base; long; straight. Color (when young)—Green and red. Position—Irregular.

*Prickles.*—Quantity—On main stalks—None. On laterals—None.

*Short needles.*—Quantity—On main stalks—None. On laterals—None.

I claim:

1. A new and distinct variety of rose plant of the hybrid tea class, substantially as herein shown and described, characterized particularly as to novelty by the unique combination of a vigorous and well-branched habit of growth, attractive green foliage, with the new foliage being darker in color than in the parent variety, "King's Ransom," and being Victoria Lake in color, a free blooming habit throughout the season, and an ovid bud form, said buds being basically yellow in color but heavily overlaid with Garnet Brown as the sepals unfold, and opening to high-centered flowers of pale Lemon Yellow color in the half-open stage, and said flowers maintaining a distinctive and attractive pale yellow color as they fully open.

No references cited.

R. E. BAGWILL, Primary Examiner